United States Patent
Wang

[11] Patent Number: 6,135,838
[45] Date of Patent: Oct. 24, 2000

[54] METHOD OF MAKING UV LAMP FOR AIR CLEANING

[75] Inventor: Wei-Hong Wang, Tao Yuan, Taiwan

[73] Assignees: Chung Shan Institute of Science and Technology, Tao Yuan; Taiwan Fluorescent Lamp Co., Ltd., Taipei, both of Taiwan

[21] Appl. No.: 09/167,587

[22] Filed: Oct. 7, 1998

[51] Int. Cl.[7] .................................................. A61L 9/20
[52] U.S. Cl. ............................................................ 445/22
[58] Field of Search ................................................ 445/22

[56] References Cited

U.S. PATENT DOCUMENTS 5,933,702  8/1999  Goswami ............................. 422/186.3

Primary Examiner—Kenneth J. Ramsey
Attorney, Agent, or Firm—Rosenberg, Klein & Lee

[57] ABSTRACT

The invention relates to a method for fabricating a UV lamp for treating waste gas and to a UV lamp for treating waste gases fabricated therefrom, which is designed and fabricated based on solgel coating techniques by coating a sol of photocatalytic materials comprising anatasse $TiO_2$ as the main component, and/or other semi-conductive components such as $WO_3$, $ZnO$, $SnO_2$, or $Fe_2O_3$, on a glass-fiber-cloth, and/or then impregnate this cloth with oxidation catalyst of precious metal such as Pd, Au, Pt or Ag, or transition metal oxide about Mo, Nb, B, Ce or Cr, and then wrap this cloth on a UV lamp. The invention relates also to a process for treating waste gases by using said UV lamp for treating waste gas through irradiating UV light therefrom on the surface of such photocatalytic materials to generate free electron and electron hole pairs which can decompose waste gases such as organic or inorganic pollutants in the air into unharmful gases.

7 Claims, 7 Drawing Sheets

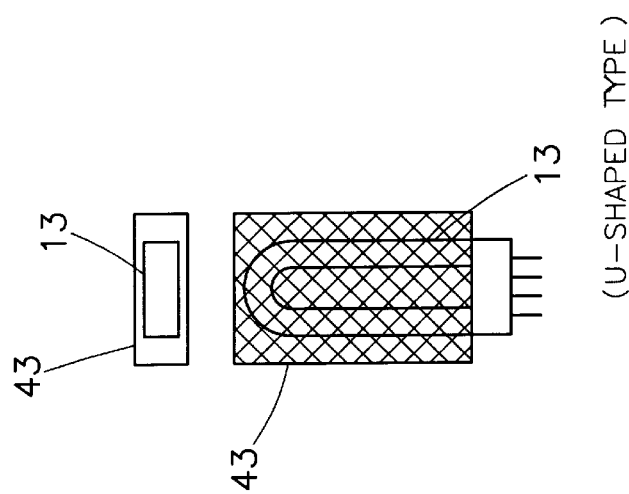
FIG. 3C (U-SHAPED TYPE)
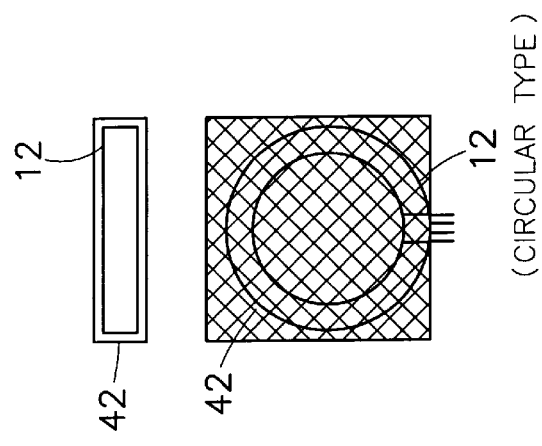
FIG. 3B (CIRCULAR TYPE)
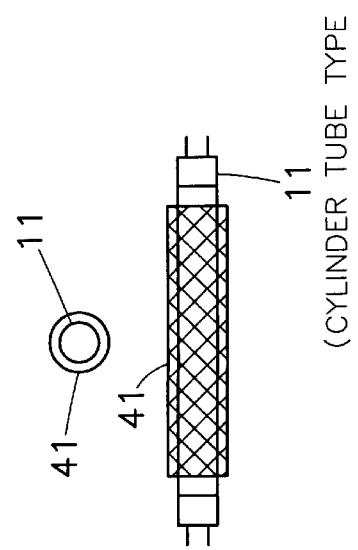
FIG. 3A (CYLINDER TUBE TYPE)

METHOD OF MAKING UV LAMP FOR AIR CLEANING

BACKGROUND OF THE INVENTION

1. Field of the Invention

The invention relates to a method for fabricating a UV lamp for treating waste gas and to a UV lamp for treating waste gases fabricated therefrom, which is designed and fabricated based on solgel coating techniques by coating a sol of photocatalytic materials on a glass-fiber-cloth, and/or then impregnate this cloth with oxidation catalysts and finally, wrap and fix this cloth on a UV lamp. The invention relates also to a process for treating waste gases by using said UV lamp for treating waste gas through irradiating UV light therefrom on the surface of such photocatalytic materials to generate free electron and electron hole pairs which can decompose waste gases such as organic or inorganic pollutants in the air into unharmful gases.

2. Description of the Prior Art

Solgel techniques have been emphasized today by technically advanced countries for several main reasons, namely, when developments of traditional chemical and physical technologies met bottlenecks, and in particular, when inorganic materials produced through traditional techniques can no longer satisfy requirements, especially, for thin film coating, materials having multiple components and special structures that can not coated by conventional physical and/or chemical method, as well as when coating those material on irregularly curve surfaces can not been achieved by conventional evaporating disposition techniques, the solgel technique, on the other hand, can easily generate a metal oxide film thereon, and at the same time, it is the characteristic feature of the solgel technique that the photocatalytical film obtained thereby has a porous crystallite structure required by the photocatalytical action. Therefore, solgel coating techniques become one of the most interesting techniques for research and development in the latter part of the twentieth century.

Recently, preparation of catalysts by solgel techniques also received emphasis by chemical industries, and in particular, photocatalytic techniques is the most important one, including the early developed photocatalytic powders for treating waste water, such as, for example, Robat A. Clyde, U.S. Pat. No. 4,446,236; Robat E. Hetrick, Ford Motor Company, U.S. Pat. No. 4,544,470; Yashiaki Harada et al., Osaka Gas Company, U.S. Pat. No. 4,699,720; Tomoji Kawai, et al., Nomura Micro Science Co., U.S. Pat. No. 4,863,608; David G. Ritchie, U.S. Pat. No. 5,069,885; Gerald Cooper, et al., Photo Catalytics Inc., U.S. Pat. Nos. 5,116,582; 5,118,422; 5,174,877; and 5,294,315; Adam Heller, et al., Board of Regents, The University of Texas System, U.S. Pat. No. 5,256,616; Ali Safarzedeh-Amiri, Cryptonics Corporation, U.S. Pat. No. 5,266,214; Fausto Miano & Borgarello, Eniricerche S.p.a., U.S. Pat. No. 5,275,741; Nancy S. Foster et al., Regents of the University of Colorado, U.S. Pat. No. 5,332,508; Ivan Wlassics et al., Ausimont S.p.a., U.S. Pat. No. 5,382,337; Paul C. Melanson & James A. Valdez, Anatol Corporation, U.S. Pat. No. 5,395,522; Henry G. Peebles III et al., American Energy Technology, Inc., U.S. Pat. No. 5,449,466; Brain E. Butters & Anthony L. Powell, Purific Environmental Technologies, Inc., U.S. Pat. Nos. 5,462,674; 5,554,300; and 5,589,078; Yin Zhang, et al., Board of Control of Michigan Technology University, U.S. Pat. No. 5,501,801; Clovis A. Linkous, University of Central Florida, U.S. Pat. No. 5,518,992; and Eiji Normura & Tokuo Suita, Ishihara Sanyo Kaisha Ltd., U.S. Pat. No. 5,541,096.

The above-mentioned U.S. patents relate chiefly to water treatments, which in the case of granular catalysts, a filtration recovering apparatus is invariably used, and it is of the most importance that such photocatalysis needs sufficient dissolved oxygen in water, otherwise, an aerating operation must carry out for supplying oxygen required by the photocatalytic degradation.

Since then, photocatalysts were used also for treating waste gases, such as those described in, for example, Gregory B. Roupp & Lynette A. Dibble, Arizona State University, U.S. Pat. No. 5,045,288; Jeffrey g. Sczechowski et al., The University of Colorado, U.S. Pat. No. 5,439,652; William A. Jacoby & Danial M. Blake, U.S. Pat. No. 5,449,443; Zhenyyu Zhang & James R. Gehlner, Inrad, U.S. Pat. No. 5,468,699; and Franz D. Oeste, Olga Dietrich Neeleye, U.S. Pat. No. 5,480,524.

The above-mentioned patens relate originally to treatment of waste gases, and basically, were carried out in a closer reactor, and therefore, utilization or operation of granular catalysts or catalysts coating granules usually needed, in general, complicate equipments.

The above-described disadvantages made the prior art photocatalysts difficult to apply on polluted air treating in our living environment, and among them, the only one waste water and/or waste gases disposal photocatalytic reactor comprising a UV lamp wrapped with photocatalysts coated film having fibers as supports thereof was the one described in Michael K. Robertson & Robert G. Henderson, Nutech Energy Systems Inc., U.S. Pat. No. 4,982,712. As above mentioned, such reactor was a closed type one such that counter flowing of gases must be forced by a blower which made such reaction system being inconveniently practice in our living environment.

As for UV lamp for treating waste gases, it is generally based on the sustained oxidative degradation against organic and/or inorganic hazardous materials in the air by a photocatalytic reaction to render them into nonharmful substances such as water or carbon dioxide. Since photocatalytic reaction took place on the catalyst through UV irradiating on hazardous waste gases and oxygen, it is inactive in case that UV light can not reach the catalyst. Accordingly, only the catalyst in the extremely thin top layer (less than one micron) that received UV light becomes active under such conditions. Therefore, in practice, it is used to employ a film coating of photocatalyst on carry substrate materials which are transmittable by UV or light to prepare a photocatalyst film.

Photocatalytic action can be effected only in case of direct UV irradiation on coating, while it is inactive in case of backside irradiating. The reason therein relates to the fact that electron hole pairs generated during UV irradiating on the surface of photocatalyst will combine in extremely short time period (microseconds) and release thermal energy before reacting with oxygen and/or materials to be reacted.

Nevertheless, a photoelectric-chemical catalyst having an electroconductive layer incorporated in the coating film structure can transfer electron generated during UV irradiating via the conductor therein to the positive electrode, such that the electron hole can be retained and the persisting time period of reactive positions can be postponed and thereby improves the efficiency of UV irradiation. However, such coating film is not easy to fabricate and practice. Consequently, it is essential for photocatalytical reaction to take place in simultaneous presence of oxygen, moisture, reactants and catalysts as well as in combination with UV irradiation to give rise the oxidative degradation.

Since the effective thickness of photocatalysts is extremely small, it is sufficient for a layer of photocatalytical material having a thickness of less than 1 micron to be deposited on UV transmittable substrate by a solgel coating technique. Because photocatalytical materials are in general metal oxides, it is conventional to use vacuum deposition, redox plating, and aqueous precipitation/adsorption coating techniques to form a thin film. Among them, the vacuum deposition technique is usually employed for depositing on the surface of a flat structure, which can not meet the practical requirement in this field. Furthermore, since vacuum deposition is not capable of obtaining a porous structure of catalysts and a crystalline structure having photocatalytical action, it becomes useless therefor. The aqueous precipitation/adsorption coating technique consists of precipitating a photocatalytical metal oxide on the surface of a substrate, however, because the bonding strength between the catalyst thus adsorbed and the surface of the substrate is generally not strong enough, the coating peels easily and is not durable. As for the redox plating, titanium metal or alloy thereof has been used to form a titanium dioxide thin film under oxidation condition at high temperature, however, since the substrate is an opaque metal and the surface area of the catalyst film thus obtained is insufficient, the photocatalytical efficiency is poor to be practical.

As sated previously, since the solgel coating technique can generate easily a coating film on an irregular surface structure as well as can produce a porous crystallite structure required by the photocatalytical action, and also from the view of the inherent feature of the photocatalytical reaction, the present inventors adopt the solgel coating technique for fabricating the UV lamp for treating waste gases according to the invention.

As for the solgel coating technique, in general, a metal alkoxide such as $Ti(OR)_4$, wherein R is a hydrocarbyl group, $C_nH_{2n+1}$, where n=1~5, and is, for example, methyl, ethyl, n-propyl, isopropyl, n-butyl, t-butyl, sec-butyl, pentyl and the like; is used as the main component in admixture with organic and/or inorganic salts of other metals such as W, Zn, Sn, and Fe and undergoes hydrolytic condensation in an alcohol solvent to form an organic metal polymer which is dissolved in that alcohol solution as a sol. Amounts of alkoxide, water, additives and solvent can be adjusted depending to the requirement of coating to form the desired film.

As the substrate used in the solgel coating technique, glass fiber woven cloth can provides an increased surface area of photocatalysts and can allow waster gases in the air diffuse readily in the photocatalytic active sites. The glass fiber woven cloth can be the one conventionally used in production of the printing circuit board, which, in general, has a fiber diameter of 10~100$\mu$, fiber number of 1~10, and porosity of 100~1000 mesh. The glass fiber woven cloth can be reinforced with a silane. In addition to the glass fiber, other materials such as quartz, ceramics or metal can be used as the substrate.

Then, the glass fiber cloth can be impregnated batchwise or continuously with the photocatalyst sol by a roller, wherein, through controlling the drawing speed of the cloth and the humidity and temperature in the air, an uniform layer (0.1~1.0$\mu$) of photocatalyst coating can be applied on the surface of the glass fiber cloth. The coated fiber cloth is undergone a hydrolysis in the air for 1~10 minutes, baked at a temperature of 100~200° C. for 10~30 minutes, sintered at high temperature of 400~600° C. for 10~120 minutes and thereafter, cooled for 10~120 minutes to a temperature below 200° C. to produce a photocatalyst-coated glass fiber cloth.

In the production of the above-described photocatalyst-coated glass fiber cloth, in order to improve the efficiently of treating waste gases, it can be soaked with a aqueous solution containing metal salts having oxidative catalytic action. Such metal salts include precious metal such as inorganic salts of Pd, Pt, Au and Ag or inorganic salts of transition metal such as Mo, Nb, V, Ce or Cr. The glass fiber cloth is ready for use after being soaked with oxidative catalyst after dried.

For use of the above-said photocatalyst and/or oxidative catalyst-coated glass fiber cloth in production of the UV lamp for treating waste gases, they can be tailored into a size depending on the length or size of the UV lamp and the number of wrapping layer required. In general, the number of layer is to achieve an UV blocking of above 99%, and normally, is 2~3 layers. After wrapping around the UV lamp, it is fixed by UV resistant glue, or seamed by laser sintering.

Suitable UV lamp is the common UV lamp, including those having wavelength of 254, 312 or 365 nm. Among them, UV lamps having wavelength of 254 and 312 nm should employ $SiO_2$ quartz and thus have high production costs, whereas the one having wavelength of 365 nm can be produced with soda lime glass tubes and has a low cost. Depending on the type of waste gases treatments, a UV lamp of 254 nm can be used for the case requiring higher energy for degrading waste gases and those of 365 nm can be used for the photocatalytic degradation of common waste gases. The UV of 365 nm is known as mosquito-capturing lamp, whereas the UV lamp of 254 nm is known as sterilizing lamp. Therefore, if the 365 nm UV lamp is wrapped with topical or a single layer of a photocatalyst-coated glass fiber cloth, it can function both as waste gas treating and mosquito-capturing; whereas the 254 nm UV lamp is wrapped with topical or a single layer of a photocatalyst-coated glass fiber cloth, it can function both as waste gas treating and sterilization.

SUMMARY OF THE INVENTION

Accordingly, in one aspect, the invention provides a process for coating photocatalyst on a glass fiber woven cloth, which comprising (1) formulating a photocatalyst coating-forming sol; (2) dip coating a glass fiber cloth with a photocatalyst sol; (3) drying and sintering into a coating having photocatalytic function; (4) impregnating said photocatalyst-coated glass fiber cloth with a solution of an oxidation catalyst; and (5) drying again to form a photocatalyst-coated glass fiber cloth.

In another aspect, the invention provides a process for fabricating a UV lamp for treating waste gas, which is designed and fabricated through solgel techniques by coating photocatalytic materials on a quartz-or glass-fiber-cloth, sintering this photocatalytic material-coated fiber cloth at high temperature into a structure having photocatalytic action, and then wrapping this cloth on a UV lamp.

In still another aspect, the invention provides a UV lamp for treating waste gases, which is fabricated by the above-described process.

In yet another aspect, the invention provides a method for treating waste gases in the air by using the above-said UV lamp through irradiating UV light on the surface of such photocatalytic materials to generate free electron and electron hole pairs which can decompose waste gases in the air into harmless products.

BRIEF DESCRIPTION OF THE DRAWINGS

The invention, as well as its many advantages, may be further understood by the following detailed description and drawings in which:

FIGS. 3A, 3B and 3C are a schematic illustration showing the wrapping of UV lamp having different shape with the photocatalyst-coated glass fiber woven cloth according to the invention;

Figure 1A:
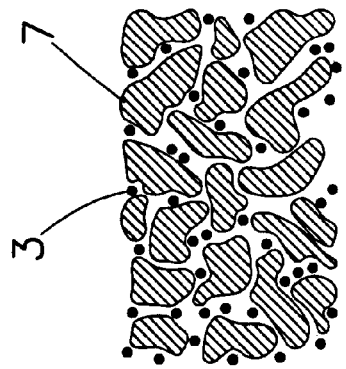
FIGS. 1A, 1B, and 1C are the schematic illustration showing the structure of the photocatalyst thin coating on the surface of the photocatalyst-coated glass fiber according to the invention.

Meanings of number and symbols in drawings are as follow:

1. glass fiber
2. photocatalyst coating
3. oxidative catalyst microparticles
4. glass fiber woven cloth
5. glass fiber yarn bundle
6. micro pore in the photocatalyst-coated layer
7. anatase $TiO_2$ photocatalyst crystal
8. outer sleeve of a lamp
11. cylinder tube type of a UV lamp
12. circular type of a UV lamp
13. U-shaped type of a UV lamp
21. air
22. waste gases
23. water
24. carbon dioxide
25. other gases
41. photocatalyst-coated glass fiber woven cloth
42. photocatalyst-coated glass fiber cloth covering box
43. photocatalyst-coated glass fiber cloth sleeve
111. quartz glass tube
112. soda lime glass tube
113. heating filament in a UV lamp
114. UV lamp pins
115. aluminum tube base of a UV lamp
116. transparent adhesive film
117. fast drying UV glue
411. UV lamp tube wrapped with a photocatalyst-coated glass fiber woven cloth around the whole tube
412. UV lamp tube wrapped with a photocatalyst-coated glass fiber woven cloth around a part of the tube

DETAILED DESCRIPTION OF THE PREFERRED EMBODIMENT

As stated above, in one aspect, the invention provides a process for coating photocatalyst on a glass fiber woven cloth, which comprising (1) formulating a photocatalyst coating-forming sol; (2) dip coating a glass fiber cloth with a photocatalyst sol; (3) drying and sintering into a coating having photocatalytic function; (4) impregnating said photocatalyst-coated glass fiber cloth with a solution of an oxidation catalyst; and (5) drying again to form a photocatalyst-coated glass fiber cloth.

The photocatalyst sol used in the above-said process for coating photocatalyst on a glass fiber woven cloth contains as the main component a metal alkoxide such as $Ti(OR)_4$, wherein R is a hydrocarbyl group, $CnH_{2n+1}$, where n=1~5, and is, for example, methyl, ethyl, n-propyl, isopropyl, n-butyl, t-butyl, sec-butyl, pentyl and the like; in a solvent such as alcohols, for example, ethanol, isopropanol, butanol, pentanol and the like. Amount of water added should be controlled to a $H_2O/Ti(OR)_4$ mol ratio of 0.5~2. Suitable amount of organic acid such as formic acid, acetic acid, propionic acid and the like, can be added as modifier and HCl or $hNO_3$ is used to adjust pH thereof in a range of 1.0~3.0. Then, after reacting under stirring and heating, a $TiO_2$ sol can be obtained. The concentration of the $TiO_2$ sol can be adjusted with alcohol solvent to a suitable range of 1~10 wt %.

The thus-formed $TiO_2$ sol can be incorporated with other photocatalytic components including $WO_3$, ZnO, $SnO_2$, and $Fe_2O_3$ which can be added as organic and/or inorganic salts thereof. The inorganic salts thereof can be halides and nitrates, whereas the organic salts can be acetates and acetoacetonate provided that they are soluble in the alcohol solvent. The alcohol solution obtained after dissolving completely can be evaporated to remove water and then redissolved by adding alcohol solvent to form a precursor alcohol solution of $WO_3$, ZnO, $SnO_2$, and $Fe_2O_3$. Addition of the MOx precursor alcohol solution is desired amount to lead to a weight ratio of $MOx/TiO_2$=1~100% results in a photocatalyst coating forming sol.

The thus-formed photocatalyst coating-forming sol can be used then to apply on a substrate such as glass, ceramics, carbonaceous materials or metal, which, preferably, are transparent and in fibrous shape. In one embodiment of the invention, the substrate is a fiber or a fiber bundle. The solgel coating technique can apply directly on the fiber or fiber bundle, while it can apply after weaving of the fiber. Since, after solgel coating and sintering, the fiber and fiber bundle can be bonded directly by an adhesive into an useful nonwoven, otherwise, they might be damaged by weaving machine during weaving after solgel coating. Therefore, it is desirable to solgel coating on fiber woven cloth and sintered to fabricate the desired photocatalyst-coated fiber cloth.

The drying and sintering in the solgel coating process according to the invention can be carried out conventionally, such as, impregnating the glass fiber cloth batchwise or continuously with the photocatalyst sol by a roller, wherein, through controlling the drawing speed of the cloth and the humidity and temperature in the air, an uniform layer (0.1~10μ) of photocatalyst coating can be applied on the surface of the glass fiber cloth. The coated fiber cloth is undergone a hydrolysis in the air for 1~10 minutes, baked at a temperature of 100~200° C. for 10~30 minutes, sintered at high temperature of 400~600° C. for 10~120 minutes and thereafter, cooled for 10~120 minutes to a temperature below 200° C. to produce a photocatalyst-coated fiber cloth.

In order to improve the capacity and efficiency of photocatalyst coating on treating waste gases, such as those containing organic substances having halogen, nitrogen, phosphorus and sulfur elements, the photocatalyst must be incorporated with oxidation catalysts. Suitable oxidation catalysts can be those commonly used, including such as, precious metal type and transition metal type. The precious metal type is usually presented as elemental state, such as, for example, Pd, Pr, Au or Ag, whereas the transition metal type is presented as metal oxides such as, for example, $MoO_3$, $Nb_2O_5$, $V_2O_5$, $CeO_2$ or $Cr_2O_3$. The amount of such oxidation catalysts in the photocatalyst is in a range of 018 10.0 wt %. Because such oxidation catalyst itself exhibits an ability of oxidizing waste gases in the air as well as can capture free electrons, electron hole pairs or active radicals generated from the action of the free electrons and electron hole pairs on $O_2$ and $H_2O$, such as, .OH, $H^+$, $.O_2^-$, $HO_2.$, $OH^-$ and the like which are released subsequently for oxidative degrading waste gases as they approached, such that the existing time period of electron hole and free electrons can be sustained and thereby improve the capacity and efficiency of the photocatalysts.

According to the process of the invention, the addition of oxidation catalyst is carried out, after solgel coating a photocatalyst on the fiber woven cloth, by impregnating the cloth with a solution of oxidation catalytic metal salt. Since the fiber woven cloth itself has a meso-pores and the photocatalyst coating has many micro pores, when the photocatalyst-coated fiber cloth is dipped in the solution of metal salts, the oxidation catalytic metal salts will be adsorbed in the meso pores within the fiber cloth and/or be absorbed in the micro-pores within the photocatalyst coating, which, after evaporating the solvent, has many fine metal salts remained on the fiber cloth and thus accomplishes the process of incorporation of oxidation catalysts in the photocatalyst-coated fiber cloth.

under irradiation of UV light, this layer of photocatalyst coating will generate free electron hole pairs. Oxygen and water on the surface of the catalyst will receive such electron hole pairs and become in an metastable state having oxidizing ability. When these ions in a metastable state having oxidizing ability encounter the organic or inorganic gases in the air, a chemical binding and degradation reaction will take place immediately. Under constantly supplying of those ions, the hazardous waste gases in the air will be degraded into unharmful gases which consist mainly of carbon dioxide and water. This photocatalytic reaction mechanism can be illustrated as follow:

  (1)

  (2)

  (3)

  (4)

  (5)

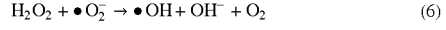  (6)

  (7)

  (8)

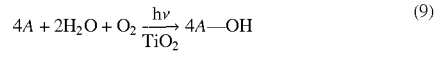  (9)

The above-mentioned reaction equations can be balanced into $(1)\times3+(2)\times2+(3)\times3+(4)\times2+(5)+(6)+(7)+(8)\times4=(9)$.

From equation (9), by way of example, when waste gas (A) is reacted firstly with .OH, 4 moles of waste gas require 2 moles of water and one mole of oxygen. Thus, this indicates that photocatalytical reaction needs absolutely both of water and oxygen. This conclusion is supported by the fact that, in the case of photocatalytic hydrolysis of organic materials in water, the reaction efficiency in the aqueous solution lack of dissolved oxygen is poor, and likewise, the reaction efficiency in air lack of moisture is also poor. Unless, subsequent to the photocatalytic degradation of waste gases in air, the product contains water or substances that can react with $h^+$ in a manner analogous to water and thereby forms .OH and $H^+$, the reaction mechanism can proceed continuously.

In another aspect, the invention provides a process for fabricating UV lamp for treating waste gases which, as described above, is designed and fabricated through solgel techniques by coating photocatalytic materials on a quartz- or glass-fiber-cloth, sintering this photocatalytic material-coated fiber cloth at high temperature into a structure having photocatalytic action, and then wrapping this cloth on a UV lamp.

In order to improve the efficacy of the UV lamp, and to not allow the UV and visible light generated by the UV lamp being absorbed by opaque materials such that the function of treating waste gases can not be provided, in one embodiment of the invention, quartz or glass fiber materials are used as the substrate. Among them, quartz lass is a material consisting of $SiO_2$ which is transmittable by the UV light having wavelength of 254 nm, 312 nm and 365 nm derived from the UV lamp, while common glass is transmittable only by UV light of 365 nm. If the activation energy for degrading waste gases is high, it is preferably to adopt UV lamps of 254 nm or 312 nm in conjunction with quartz glass fiber woven cloth as the supporting substrate of photocatalysts. With respect to the common organic waste gases, a UV lamp of 365 nm wavelength is sufficiently used in combination with common glass fiber woven cloth as the substrate. Thus, when the UV lamp illuminates on the photocatalyst-coated glass fiber woven cloth, a portion of the light will be absorbed, a portion reflected and a portion be transmitted, wherein reflected and transmitted portions can be absorbed subsequently by the photocatalyst coating till completely absorbed for proceeding of photocatalytical degradation of waste gases.

Figure 1B:
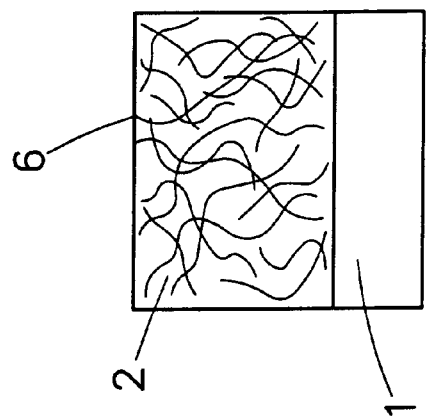
Figure 1C:
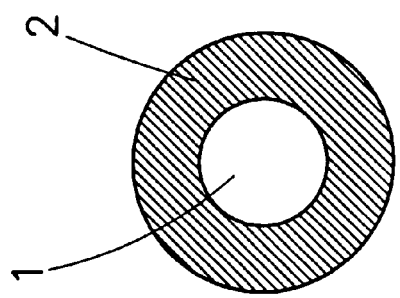

Now, referring to FIGS. 1A–C, the structure of the photocatalyst thin coating on the surface of the photocatalyst-coated quartz or common glass fiber prepared by the above-described solgel coating process according to the invention and impregnated with oxidation catalysts will be illustrated as follow: if a single glass fiber <1> was photocatalyst-coated <2>, as shown in FIG. 1(A), there are tine interstitial pathway <6> surrounding the anatase $TiO_2$ crystal <7> within the coating, as shown in FIG. 1(B), and a plurality of fine oxidation catalysts are adsorbed on the surface of the coating as well as in the internal interstitial pathway, as shown in FIG. 1(C).

Figure 2C:
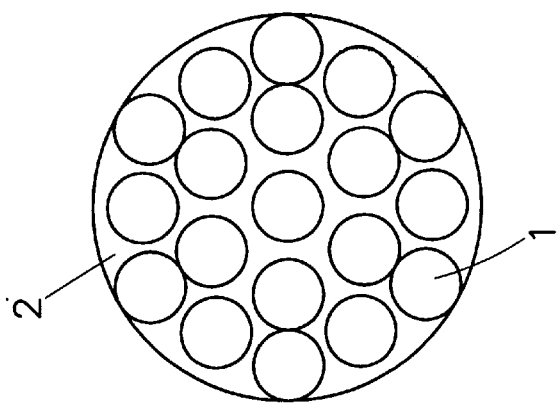
FIGS. 2A, 2B and 2C are a schematic illustration showing the process of wrapping a UV lamp with the photocatalyst-coated glass fiber woven cloth according to the invention.
Figure 2B:
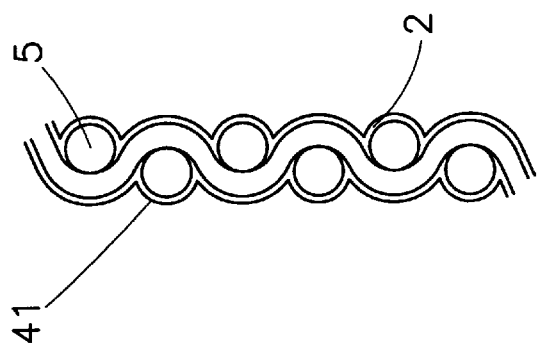
Figure 2A:
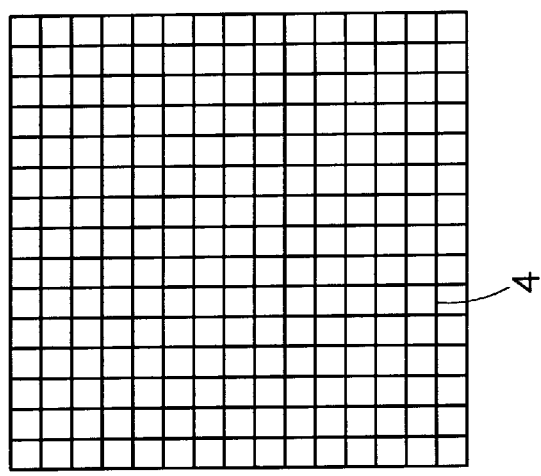

If a bundle consisting a number of glass fibers <5> has been photocatalyst-coated <2>, as shown in FIG. 2(C), similarly, there are likewise anatase $TiO_2$ crystals <7> and tine interstitial pathways <6> within the structure of the photocatalyst coating, and there are a plurality of fine oxidation catalysts <3> absorbed on the surface of the coating as well as in the inner interstitial pathways. If a glass fiber woven cloth <4> has been photocatalyst-coated <2>, as shown in FIG. 2(A), a photocatalyst-coated glass fiber woven cloth <41> is obtained, as shown in FIG. 2(B), there are again anatase $TiO_2$ crystals <7> and tine interstitial pathways <6> within the structure of the photocatalyst coating, and there are a plurality of fine oxidation catalysts <3> absorbed on the surface of the coating as well as in the inner interstitial pathways.

Now, referred to FIGS. 3A–C, as one aspect of the invention, the fabrication of the UV lamp for treating waste gases according to the invention will be explained below. The UV lamp for treating waste gases according to the invention is fabricated by wrapping around a UV lamp tube with a photocatalyst-coated glass fiber woven cloth in a manner as winding type, covering box type or sleeve type, as shown in FIG. 3. In case of using linear UV lamp tube <11>, one or two round of a photocatalyst-coated glass fiber cloth <41> are wound plainly around the tube and fixed on the glass tube by applying on both end and the edge with adhesives such as UV light resistant silicone type adhesives or glass cement, such as shown in FIG. 3(A).

In the case of circular UV lamp tube <12>, the photocatalyst-coated glass fiber cloth can be tailored into a covering box <42> and cover the box on the circular UV lamp tube, as shown in FIG. 3(B). While in the case of U-shaped UV lamp tube <13>, the photocatalyst-coated glass fiber cloth can be tailored into a sleeve <43> and slip the sleeve <43> on the U-shaped UV lamp tube, as shown in FIG. 3(C).

Figure 4A:
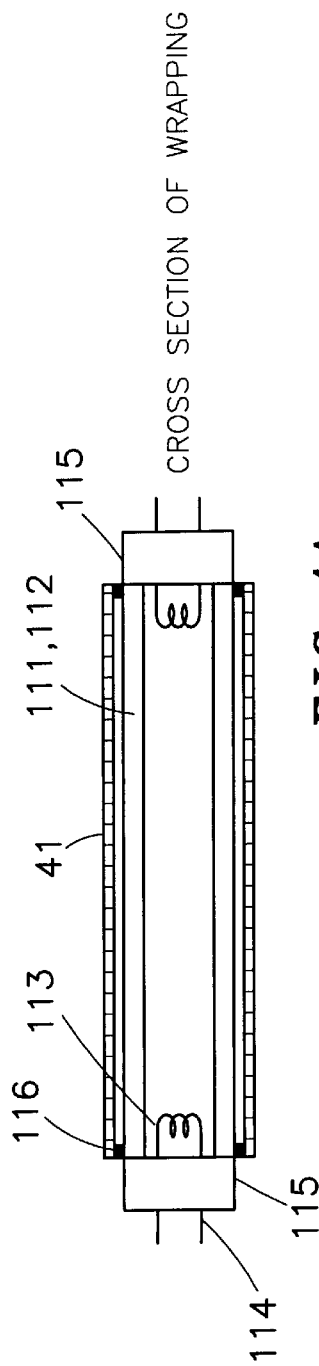
FIGS. 4A, 4B and 4C are a schematic illustration showing different wrapping mode on UV lamp for treating waste gases with the photocatalyst-coated glass fiber woven cloth according to the invention.
Figure 4B:
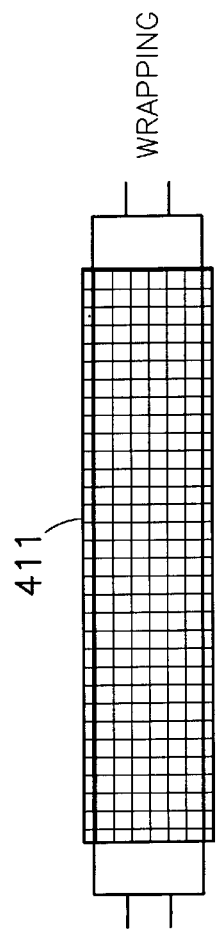
Figure 4C:
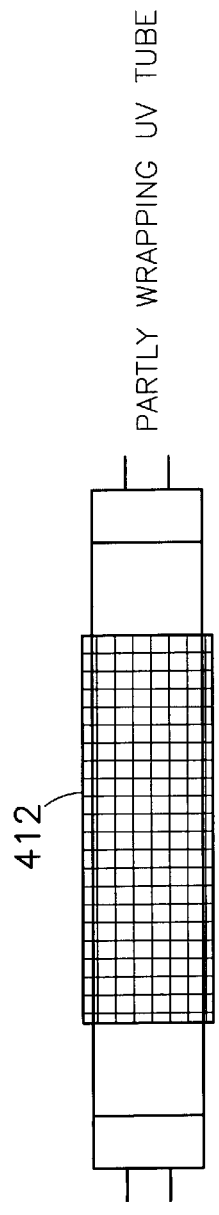

Furthermore, in order to retain the original function of the UV lamp, the UV lamp tube can be wrapped with the photocatalyst-coated glass fiber cloth on a part thereof, such as in a manner of <412> shown in FIG. 4(C), such that, for example, the 365 nm UV lamp which uses soda lime glass tube <112> can thereby have both functions of waste gas treatment and mosquito-capturing, while the partly wrapped 254 nm or 312 nm UV lamp which use quartz glass tube <111> can thereby have both functions of waste gases treatment and sterilization.

Figure 5C:
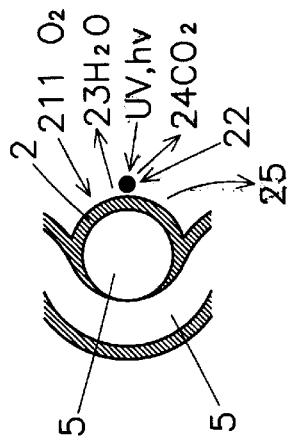
FIGS. 5A, 5B and 5C are a schematic illustration showing the mechanism of photocatalytic degradation of waste gases by the UV lamp for treating waste gases according to the invention.
Figure 5B:
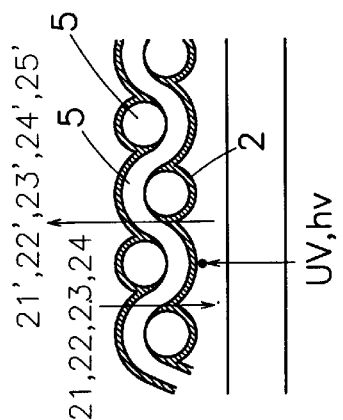
Figure 5A:
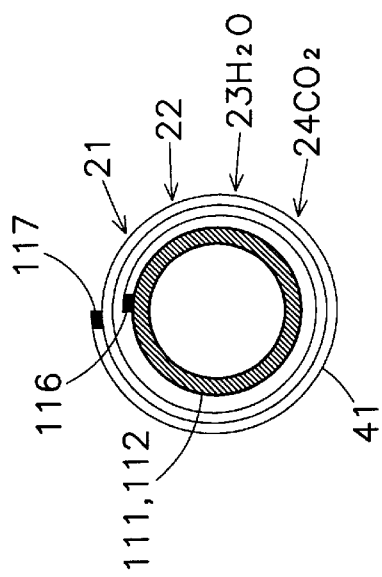

The linear UV lamp can be wrapped on whole tube with a photocatalyst-coated glass fiber cloth in a manner as <411> shown in FIG. 4(B) with its cross-section view shown in FIG. 4(A). As to the constructure of that UV lamp, a quartz glass tube <111> or soda lime glass tube <112> is vacuum sealed at both ends. The heating filaments <113> therein are filled with minor amount of mercury and are connected with external heating pins <114>. Next, the tube is sealed by cementing with tube bases <115> at both ends. Finally, the photocatalyst-coated glass fiber cloth <41> is wound around and fixed on the UV lamp by a two-sided adhesive film <116> and then sealed the edge by a quick drying UV adhesive <117>, as shown in FIG. 5(A), and thereby accomplishes the fabrication of the UV lamp for treating waste gases according to the invention.

In the fabrication of the UV lamp for treating waste gases according to the invention, the circular UV lamp tube <12> is wrapped with photocatalyst-coated glass fiber cloth box <42> and the U-shaped UV lamp tube <13> is wrapped with a photocatalyst-coated glass fiber cloth sleeve <43>, wherein these photocatalyst-coated glass fiber cloth box <42> or sleeve <43> can be made separately, and, when they are used, they can be simply placed on the UV lamp tube in a manner as described above to function.

As described above, the UV lamp for treating waste gases according to the invention is constructed by wrapping a photocatalyst-coated glass fiber woven cloth around a UV lamp tube such that, when the UV lamp is turned on in the air, a function of waste gases treatment occurs accordingly. As such, no mater whether the photocatalyst-coated glass fiber woven cloth is used to warp around a linear UV lamp <11>, a circular UV lamp <12> or a U-shaped UV lamp <13> tube, such function of treating waste gases always requires three conditions as following: (1) when turned on, UV lights of 245 nm/312 nm or 365 nm emitted by the UV lamp will transmit through the glass tube and illuminate on the photocatalyst coating; (2) there are moisture and photocatyltically degradable waste gases in the air, which can diffuse through the large interstitial pathway within the coated glass fiber woven cloth to the photocatalyst coating illuminated by the UV light; and (3) unharmful gaseous products generated by photocatyltically degrading waste gases in the air and the air itself can back diffusing through the large intersitial pathway within the coated glass fiber woven cloth into the air.

Now, as a yet another aspect of the invention, a process for treating waste gases according to the invention will be described below. In the process for treating waste gases according to the invention, the above-described UV lamp for treating waste gases is used. As the UV lamp for treating waste gases is wrapped with a photocatalyst-coated glass fiber woven cloth, the air <21> that contains organic or inorganic hazardous waste gases <22> normally contains also moisture <23> and carbon dioxide <24>, as illustrated in FIG. 5(A), which can pass from outside of the coated glass fiber woven cloth <41> into the interstitial space between the coated glass fiber cloth and the lamp tube by diffusing through the large interstitial pathway, whereupon, as the UV light emitted by the UV lamp illuminates on the photocatalyst <2>, electron hole pairs generated will combine with $O_2$ and $H_2O$ in the air to produce .OH free radical which then undergoes a oxidative degradation reaction with such hazardous waste gas <22> in the air according to the reaction equations (1) to (8) and the balanced reaction equation (9). The reaction products comprise $H_2O$ <23>, $CO_2$<24> and other gases <25>, which, in combination with some $O_2$ consumed residual air <21'>, unreacted waste gases <22'>, total moisture <23'> and total $CO_2$ <$\geq$'>, discharge out of the coated glass fiber cloth <41> by back diffusing through the large interstitial pathway within said coated glass fiber woven cloth as shown in FIG. 5(B), while the change of reactants and products occurred upon UV illuminating the photocatalyst coating <2> on the glass fiber yarn bundle <5> is illustrated in FIG. 5(C).

In one embodiment, the process for treating waste gases according to the invention comprises a open type of use of the UV lamp according to the invention, which, based on the fitting with surrounding facilities, can comprise nature convection and forced convection types, while, based on the manner of installation, can comprise horizontal and perpendicular installation types, that is, in such open types, it is unnecessary that the UV lamp for treating waste gases has to be in a closed container and the input of gases to be treated in the container and the output of gaseous products from the container must be conducted by a blower. It need simply install the UV lamp for treating waste gases, whereby, since, when the UV lamp is turned on, a heat energy from the heating filaments on both ends can transfer to the lamp tube, and, in the course of conversion of electric energy into UV light, heat energy generated from consumption of part of energy thereof can transfer also to the lamp tube, so that some definite heat energy will radiates from the lamp tube, and thereby provides energy required for nature convecting and diffusing the air.

Figure 6C:
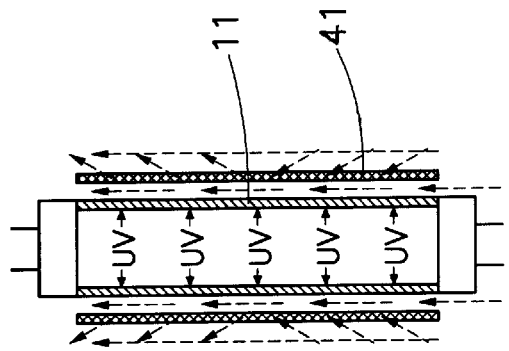
FIGS. 6A, 6B and 6C are a schematic illustration showing a open type of installation of the UV lamp for treating waste gases according to the invention, and the flowing and diffusion of waste gases under a state of nature convection.
Figure 6B:
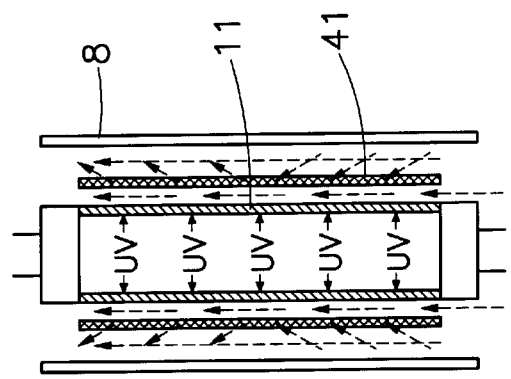
Figure 6A:
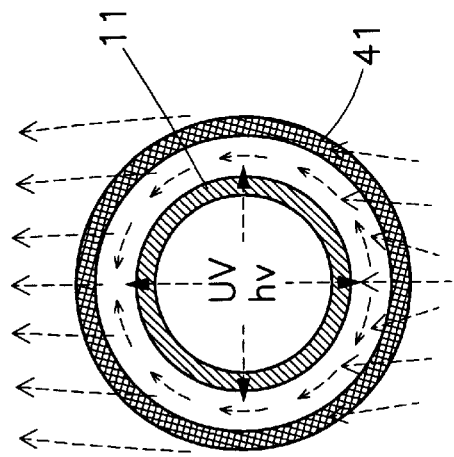

In one embodiment, the UV lamp for treating waste gases is hanged horizontally, the nature convection of air forces the air <21> beneath the UV lamp to flow upwardly and part of them diffuse into the gap between the photocatalyst-coated glass fiber woven cloth <41> and the UV lamp tube, where, after oxidative degradation by the action of the photocatalyst coating and the UV light, diffuse away the photocatalysts-coated glass fiber cloth <41>, while unreacted gases diffuses upwardly and outwardly along the gap, and finally, air <21'> in admixture with $H_2O$ <23'>, $CO_2$ <24'>, residual waste gases <2'> and gaseous reaction products <25> will diffuse upwardly and convects spontaneously out of the UV lamp; meanwhile, gases in the entire space will be continuously treated through gas diffusion and nature convection and by the action of the UV lamp for treating waste gases according to the invention, as illustrated in FIG. 6(A).

In another embodiment, the UV lamp for treating waste gases according to the invention is hanged perpendicularly, as shown in FIG. 6(C), where, the diffusion and spontaneous convection of the air, basically, are similar to those occurred in the horizontal installation. However, due to perpendicular hanging, the nature convection is stronger and the effect of gas diffusion is also stronger, and thereby provides better treating capability for waste gas. In yet another embodiment, an out sleeve <8> is provided around the UV lamp and results in better effect as illustrated in FIG. 6(B). Such outer sleeve is made of transparent material and must have an inner diameter larger than that of the UV lamp, for example, an inner diameter twice larger that the outer diameter of the UV lamp, while, has a length comparable to that of the UV lamp.

Figure 7B:
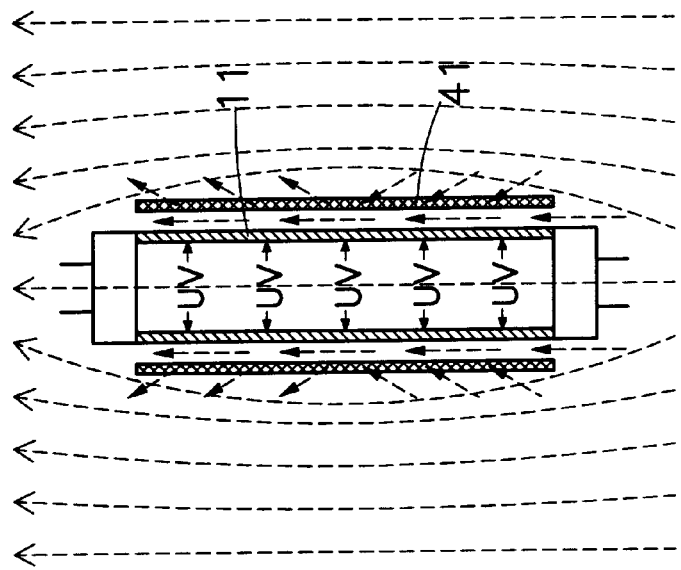
FIGS. 7A, 7B are a schematic illustration showing a open type of installation of the UV lamp for treating waste gases according to the invention, and the flowing and diffusion of waste gases under a state of forced convection.
Figure 7A:
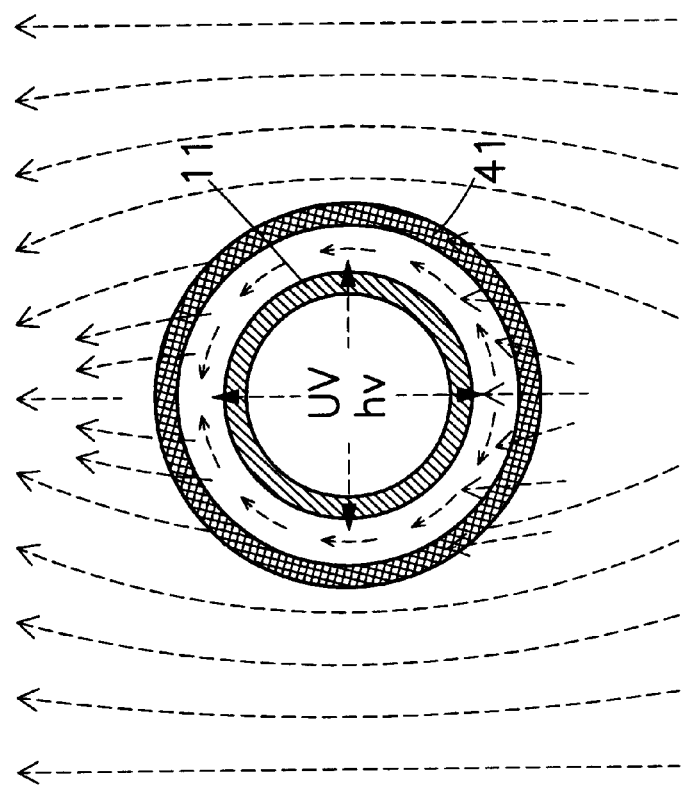

In still another embodiment, in order to arrange a forced air convection, the UV lamp for treating waste gases can be installed in an air flowing space or a conduct, such as, for example, at the outlet of an air conditioner, within the air conduct of an air conditioner, on the base of ventilator in a bathroom, and in a sewer, whereby, the efficiency of waste gas treatment can be improved by means of external forced air convection, as illustrated in FIG. 7(A)/(B).

In summary, the UV lamp for treating waste gases according to the invention can be installed in a open status, such as, simply replacing the common sunlight lamp tube with the UV lamp of the invention, whereby, when the lamp is turned on, the hazardous waste gases in air can be degraded into unharmful gases. Moreover, the UV lamp for treating waste gases according to the invention can be designed and tailor-made with respect to the requirements of various application situations, such as, air conditioning conduct in buildings, ventilation in family bathroom, refrigerator, food and dish store oven and air conditioner. Furthermore, the UV lamp of the invention can be designed and fabricated to have both the original function thereof such as mosquito-capturing and sterilization and the function of treating waste gases. In addition, the UV lamp for treating waste gases according to the invention can be used whole day, especially, at night and in dark room, where, since light source of a UV lamp tube do not emit just UV light but includes some bluish visible light also, such that it not only can be used as a low illumination lamp at night, but also can treat waste gases in air to keep the air clean.

Many changes and modifications in the above described embodiments of the invention can, of course, be carried out without departing from the scope thereof. Accordingly, to promote the progress in science and the useful arts, the invention is disclosed and is intended to be limited not only by the scope of the appended claims.

What is claimed is:

1. A method for fabricating a UV lamp for treating waste gases, comprising the steps of:

（a) formulating a photocatalyst coating sol;

（b) dip coating a glass fiber cloth with said photocatalyst sol;

（c) drying and sintering into a coating having a photocatalytic function;

（d) impregnating said photocatalyst-coated glass fiber cloth with a solution of an oxidation catalyst;

（e) drying again to form a photocatalyst-coated glass fiber cloth; and,

（f) wrapping around a UV lamp with said photocatalyst-coated glass fiber cloth, wherein depending on the shape of the UV lamp tube, said photocatalyst-coated glass fiber cloth wrap tightly and be fixed around said UV lamp tube, or said photocatalyst-coated glass fiber cloth can be tailored into a sleeve or box and then cover on said UV lamp tube.

2. A process as recited in claim 1, wherein said photocatalyst coating-forming sol containing $TiO_2$, $WO_3$, ZnO, SnO2 or $Fe_2O_3$, at least one of them being $TiO_2$ in a form as metal alkoxide of $Ti(OR)_4$, wherein R is a hydrocarbyl group, CnH2N+1, where n=1~5, and wherein, the water for hydrolysis and condensation of said photocatalyst coating-forming sol is controlled to a value suitable for preparing said photocatalyst coating-forming sol.

3. A process as recited in claim 1, wherein said solution of an oxidation catalyst comprising precious metal salts of Pd, Pt, Au, or Ag, and/or transition metal salts of Mo, Nb, V, Ce or Cr, dissolved in water or solvent.

4. A process as recited in claim 1, wherein said glass fiber cloth comprising single glass fiber or glass fiber bundle made of UV light transmittable quartz glass or soda lime glass, and said single glass fiber or glass fiber bundle being woven or melt-bonded into porous, transparent and windable glass fiber cloth.

5. A process as recited in claim 1, wherein coating said photocatalyst sol on the surface of said glass fiber cloth resulting into a chemical bonding between said photocatalyst coating and said glass fiber cloth such that said photocatalyst coating does not peel easily from said glass fiber cloth.

6. A process as recited in claim 1, wherein, after coating said glass fiber cloth with said photocatalyst sol, a solution of oxidation catalyst being sprayed on or impregnated therewith, and then drying said glass fiber cloth to allow said oxidation catalyst being absorbed or diffusing into photocatalyst such that the efficiency of treating waste gases of said photocatalyst-coated glass fiber cloth used in said UV lamp for treating waste gases is improved thereby.

7. A process as recited in claim 1, wherein the UV lamp can emit UV light having wavelength in the range of 200–400 nm, and included commonly used UV lamps emitting UV light having wavelength of 365 nm, 312 nm, and 254 nm, respectively.

* * * * *